(12) United States Patent
Mallough et al.

(10) Patent No.: US 10,463,780 B2
(45) Date of Patent: Nov. 5, 2019

(54) FLUID DEPLETION WARNING SYSTEM FOR PHACOEMULSIFICATION SURGICAL APPLICATIONS

(71) Applicant: Abbott Medical Optics Inc., Santa Ana, CA (US)

(72) Inventors: Mitchell W. Mallough, Irvine, CA (US); Abraham Hajishah, Irvine, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 0 days.

(21) Appl. No.: 14/608,927

(22) Filed: Jan. 29, 2015

(65) Prior Publication Data

US 2016/0220751 A1 Aug. 4, 2016

(51) Int. Cl.
*A61M 3/02* (2006.01)
*A61F 9/007* (2006.01)
*A61M 1/00* (2006.01)

(52) U.S. Cl.
CPC ......... *A61M 3/022* (2014.02); *A61F 9/00745* (2013.01); *A61M 1/0058* (2013.01); *A61F 9/00736* (2013.01); *A61M 1/0031* (2013.01); *A61M 2205/123* (2013.01); *A61M 2205/18* (2013.01); *A61M 2205/3389* (2013.01); *A61M 2210/0612* (2013.01)

(58) Field of Classification Search
CPC .............. A61M 3/0266; A61M 3/0233; A61M 2210/0612; A61M 2205/3331; A61M 5/172; A61M 5/1723; A61F 9/00736; A61B 2218/002
See application file for complete search history.

(56) References Cited

U.S. PATENT DOCUMENTS 5,135,485 A * 8/1992 Cohen ................ A61M 5/1684
324/606
6,491,661 B1 * 12/2002 Boukhny ............ A61M 1/0058
604/118

(Continued)

FOREIGN PATENT DOCUMENTS

EP 1900347 A1 3/2008

OTHER PUBLICATIONS

International Search Report and Written Opinion for Application No. PCT/US2015/065631, dated Mar. 29, 2016, 12 pages.

*Primary Examiner* — Jenna Zhang
(74) *Attorney, Agent, or Firm* — Johnson & Johnson Surgical Vision, Inc.

(57) ABSTRACT

A system apparatus and method for determining fluid depletion in a surgical system. A surgical system may include a surgical console, display, a processor operatively coupled to the surgical console, and a surgical cassette in fluid communication with an irrigation source and an aspiration line. Certain techniques involve the processor determining a volume of fluid in the irrigation source. The processor may be configured to receive sensed measurements regarding a rate of fluid flow over time from the irrigation source, process the rate of fluid flow relative to the determined volume and produce a first signal for the display to indicate a remaining capacity of the volume of fluid. Warnings and/or alarms may be triggered if fluid volume falls below a predetermined threshold.

20 Claims, 7 Drawing Sheets

(56) References Cited

U.S. PATENT DOCUMENTS

| | | | | |
|---|---|---|---|---|
| 8,444,592 B2* | 5/2013 | Williams | A61M 1/0058 | 604/27 |
| 8,491,528 B2* | 7/2013 | Muri | A61F 9/00745 | 604/131 |
| 2005/0181018 A1* | 8/2005 | Peyman | A61F 9/0017 | 424/427 |
| 2005/0228423 A1* | 10/2005 | Khashayar | A61M 3/0216 | 606/167 |
| 2006/0064053 A1 | 3/2006 | Bollish et al. | | |
| 2007/0005029 A1* | 1/2007 | Hopkins | A61M 1/0031 | 604/317 |
| 2008/0000485 A1 | 1/2008 | Williams et al. | | |
| 2008/0114289 A1* | 5/2008 | Muri | A61F 9/00745 | 604/30 |
| 2008/0114290 A1* | 5/2008 | King | A61F 9/00745 | 604/30 |
| 2008/0154095 A1* | 6/2008 | Stubkjaer | A61M 3/0258 | 600/156 |
| 2008/0177126 A1* | 7/2008 | Tate | A61M 5/172 | 600/5 |
| 2009/0013780 A1* | 1/2009 | Gao | A61M 1/0023 | 73/293 |
| 2009/0048607 A1* | 2/2009 | Rockley | A61F 9/00745 | 606/107 |
| 2010/0121257 A1* | 5/2010 | King | A61M 1/0058 | 604/22 |
| 2010/0125246 A1* | 5/2010 | Kalpin | A61M 5/14276 | 604/151 |
| 2010/0228222 A1* | 9/2010 | Williams | A61M 1/0058 | 604/500 |
| 2010/0249693 A1* | 9/2010 | Links | A61F 9/00736 | 604/22 |
| 2010/0280435 A1* | 11/2010 | Raney | A61F 9/00745 | 604/22 |
| 2010/0312170 A1* | 12/2010 | Maaskamp | A61M 1/0031 | 604/22 |
| 2011/0092891 A1* | 4/2011 | Gerg | A61F 9/00745 | 604/28 |
| 2011/0112472 A1* | 5/2011 | Jacobson | A61F 9/00736 | 604/67 |
| 2011/0257591 A1* | 10/2011 | Nelson Konen | A61M 5/14276 | 604/67 |
| 2012/0265144 A1* | 10/2012 | Kalpin | A61M 5/14276 | 604/140 |
| 2013/0060211 A1* | 3/2013 | Adams, Jr. | A61M 3/0283 | 604/327 |
| 2013/0123680 A1* | 5/2013 | Ha | A61M 3/0241 | 604/22 |
| 2013/0197471 A1* | 8/2013 | Williams | A61M 3/0229 | 604/500 |
| 2014/0114236 A1* | 4/2014 | Gordon | A61M 1/0031 | 604/28 |

* cited by examiner

FLUID DEPLETION WARNING SYSTEM FOR PHACOEMULSIFICATION SURGICAL APPLICATIONS

BACKGROUND OF THE INVENTION

Field of Technology

The present invention relates generally to the sensing of surgical fluid levels and/or a fluid level flow rate to determine relative remaining fluid levels and transmit warnings when fluid levels are below a predetermined threshold.

Description of the Background

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil and within a capsular bag, the capsular bag being a thin, relatively delicate structure which separates the eye into anterior and posterior chambers.

With age, clouding of the lens or cataracts is fairly common. Cataracts may form in the hard central nucleus of the lens, in the softer peripheral cortical portion of the lens, or at the back of the lens near the capsular bag. Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humor in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms may be used in phacoemulsification and other treatment systems for the eyes, aspiration flow systems can generally be classified in two categories: 1) volumetric-based aspiration flow systems using positive displacement pumps (e.g. peristaltic); and 2) vacuum-based aspiration systems using a vacuum source, typically applied to the aspiration flow through an air-liquid interface within a reservoir (e.g. Venturi). Both systems may be incorporated into one treatment system and/or cassette. Cassette ("pack") systems can be used to couple peristaltic pump drive rotors and/or vacuum systems of the surgical consoles to an eye treatment handpiece, with the flow network conduit of the cassette being disposable to avoid cross-contamination between different patients.

In traditional ophthalmic surgery, fluid from the fluid source is also used to irrigate the eye during a procedure. As mentioned above, the irrigation fluid serves to maintain proper intraocular pressure and to replace fluid during aspiration of emulsified lens fragments. The irrigation source is typically a 500 ml bottle or drip bag of saline solution. One issue is that, during ophthalmic surgery, the potential exists for the saline solution to be depleted, turning the irrigation dry. Though an unlikely scenario, the potential consequences are substantial—severe cornmeal burns, capsular tear requiring vitrectomy or additional vitro-retinal surgery, damage to the structure of the eye, and/or loss of vision.

To mitigate such occurrences, staff operating a system typically begin each procedure with a fresh irrigation source prior to each case, and monitor the fluid visually throughout surgery. In some instances, flow sensors are used to measure flow out of the irrigation source. However, conventional configurations do not efficiently provide relative irrigation source volumes and only provide warnings when a detected flow indicates a very low irrigation source volume. As such, improvements are needed in the art to address these issues.

SUMMARY

Accordingly, under one exemplary embodiment, a surgical system is disclosed, comprising a surgical console comprising a display, a processor operatively coupled to the surgical console, and a surgical cassette in fluid communication with an irrigation source and an aspiration line. The processor may be configured to determine a volume of fluid in the irrigation source, and receive sensed measurements regarding a rate of fluid flow over time from the irrigation source. The processor may be configured to process the rate of fluid flow relative to the determined volume and produce a first signal for the display to indicate a remaining capacity of the volume of fluid.

Under another exemplary embodiment, a processor-based method is disclosed for operating a surgical system comprising a surgical console comprising a display, a processor operatively coupled to the surgical console, and a surgical cassette in fluid communication with an irrigation source and an aspiration line. The method may comprise the steps of determining in the processor a volume of fluid in the irrigation source, receiving in the processor sensed measurements regarding a rate of fluid flow over time from the irrigation source, and processing the rate of fluid flow relative to the determined volume and produce a first signal for the display to indicate a remaining capacity of the volume of fluid.

DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Figure 1A:
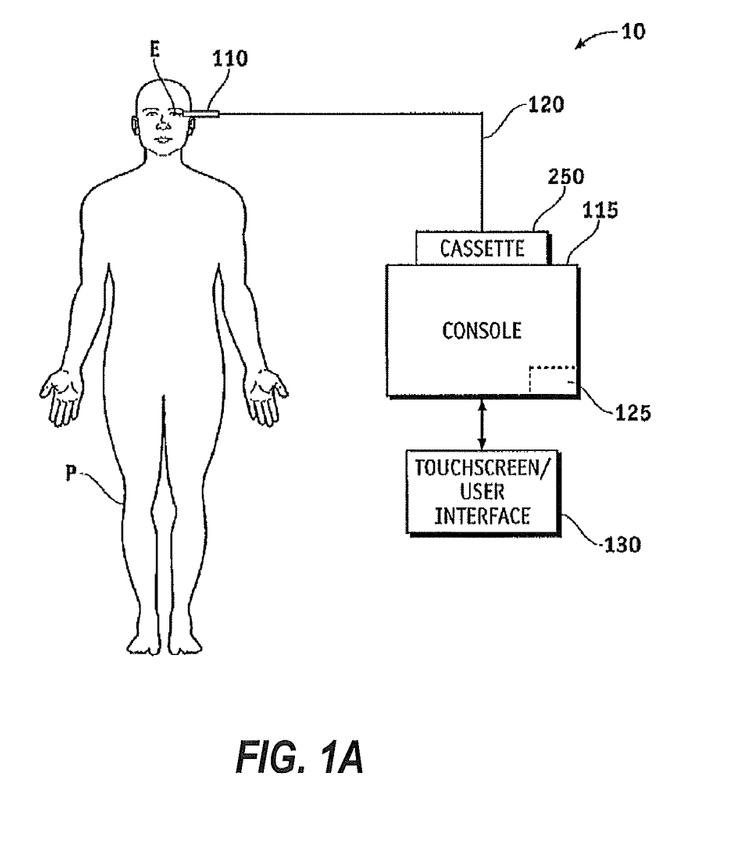
FIG. 1A is a schematic illustrating an eye treatment system in which a cassette is coupled to an eye treatment probe with an eye treatment console under one embodiment.

Referring now to FIG. 1A, a system 10 for treating an eye E of a patient P generally includes an eye treatment probe handpiece 110 coupled with a console 115 by a cassette 250. Handpiece 110 generally includes a handle for manually manipulating and supporting an insertable probe tip. The probe tip has a distal end which is insertable into the eye, with one or more lumens in the probe tip allowing irrigation fluid to flow from console 115 and/or cassette 250 into the eye. Aspiration fluid may also be withdrawn through a lumen of the probe tip, with console 115 and cassette 250 generally including a vacuum aspiration source, a positive displacement aspiration pump, or both to help withdraw and control a flow of surgical fluids into and out of eye E. As the surgical fluids may include biological materials that should not be transferred between patients, cassette 250 will often comprise a sterilizable (or alternatively, disposable) structure, with the surgical fluids being transmitted through flexible conduits 120 of cassette 250 that avoid direct contact in between those fluids and the components of console 115.

When a distal end of the probe tip of handpiece 110 is inserted into an eye E, for example, for removal of a lens of a patient P with cataracts, an electrical conductor and/or pneumatic line (not shown) may supply energy from console 115 to an ultrasound transmitter of handpiece 110, a cutter mechanism, or the like. Alternatively, handpiece 110 may be configured as an irrigation/aspiration (I/A) and/or vitrectomy handpiece. Also, the ultrasonic transmitter may be replaced by other means for emulsifying a lens, such as a high energy laser beam. The ultrasound energy from handpiece 110 helps to fragment the tissue of the lens, which can then be drawn into a port of the tip by aspiration flow. So as to balance the volume of material removed by the aspiration flow, an irrigation flow through handpiece 110 (or a separate probe structure) may also be provided, with both the aspiration and irrigation flows being controlled by console 115.

To avoid cross-contamination between patients without incurring excessive expenditures for each procedure, cassette 250 and its flexible conduits 120 may be disposable. However, the flexible conduit or tubing may be disposable, with the cassette body and/or other structures of the cassette being sterilizable. Cassette 250 may be configured to interface with reusable components of console 115, including, but not limited to, peristaltic pump rollers, a Venturi or other vacuum source, a controller 125, and/or the like.

Console 115 may include controller 125, which may include an embedded microcontroller and/or many of the components common to a personal computer, such as a processor, data bus, a memory, input and/or output devices (including a user interface 130 (e.g. touch screen, graphical user interface (GUI), etc.), and the like. Controller 125 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 125 may have (or be coupled with) a recording media reader, or the code may be transmitted to controller 125 by a network connection such as an internet, an intranet, an Ethernet™, a wireless network, or the like. Along with programming code, controller 125 may include stored data for implementing the methods described herein, and may generate and/or store data that records parameters corresponding to the treatment of one or more patients. Many components of console 115 may be found in or modified from known commercial phacoemulsification systems from Abbott Medical Optics, Inc. of Santa Ana, Calif.; Alcon Manufacturing, Ltd. of Ft. Worth, Tex., Bausch and Lomb of Rochester, N.Y., and other suppliers.

Figure 1B:
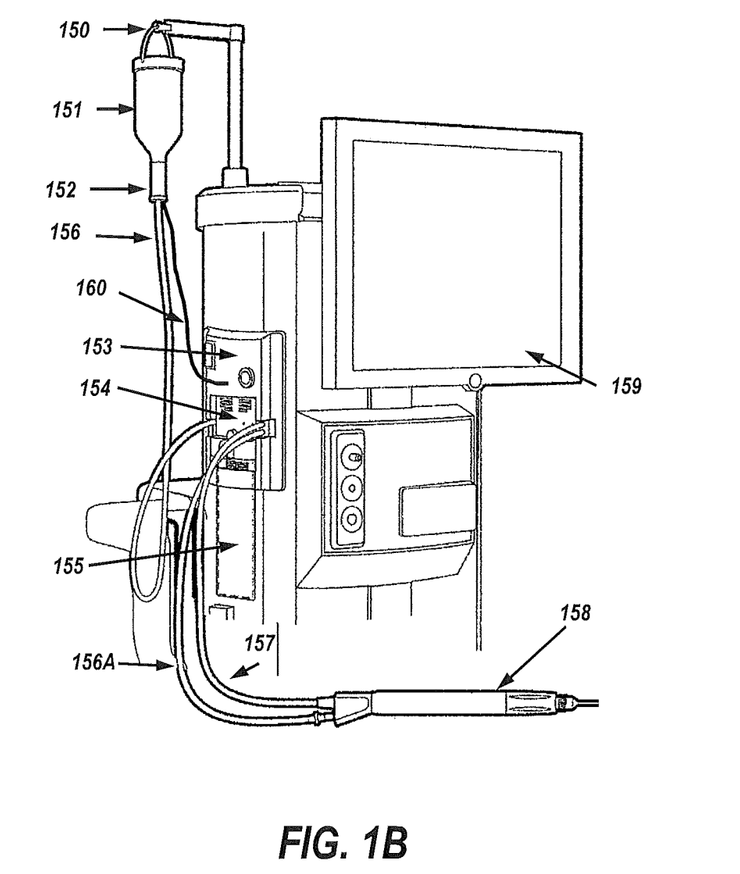
FIG. 1B is a schematic illustrating a surgical eye treatment console under another exemplary embodiment.

Referring now to FIG. 1B, a simplified surgical console is illustrated, where a fluid path may be demonstrated under an exemplary embodiment. In this example, an irrigation source 151 may be configured as a bottle or bag hanging from an IV pole hanger 150. It is understood by those skilled in the art that, while an integrated IV pole is illustrated, other configurations, utilizing standalone/static IV poles, or other suitable configurations, are contemplated by the present disclosure.

An exemplary irrigation path for fluid may be realized via tubing cassette 154 having cassette tubing interface at fluidics panel 153, which receives fluid from irrigation source 151 via drip chamber 152. Irrigation line 156A and aspiration line 157 are coupled to handpiece 158. Irrigation fluid may flow from drip chamber 152 through the irrigation tubing into tubing cassette 154. Irrigation fluid may then flow from the tubing cassette through handpiece irrigation line 156A which may be coupled to an irrigation port on handpiece 158. Aspirated fluid may flow from handpiece aspiration line 157 back to tubing cassette 154 and into a waste collection bag 155. A touch screen display 159 may be provided to display system operation conditions and parameters, and may include a user interface (e.g., touch screen, keyboard, track ball, mouse, etc.—see controller 125 of FIG. 1A) for entering data and/or instructions to the system of FIG. 1B.

Figure 2A:
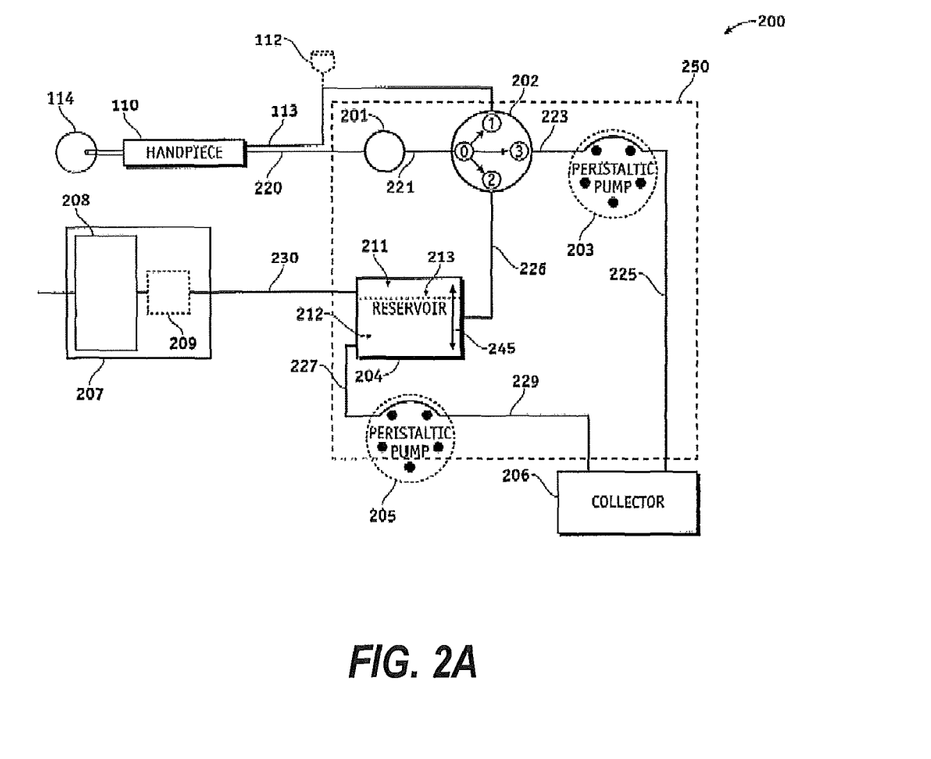
FIG. 2A is a functional block diagram of an exemplary cassette system for an eye treatment system under one embodiment.

Referring to FIG. 2A, an exemplary cassette system showing some of the components and interfaces that may be employed in a phaco system, such as ones illustrated in FIGS. 1A-B. Handpiece 110 may be connected to (or coupled with) the input side of fluid vacuum sensor 201, typically by conduits 220 which comprise fluid pathways such as fluid pathway 220. The output side of fluid vacuum sensor 201 is connected to flow selector valve 202 within cassette 250 via fluid pathway 221. The exemplary embodiment may configure flow selector valve 202 to interface between handpiece 110, balanced saline solution (BSS) fluid bottle 112, pump 203, which is shown as a peristaltic pump but may be another type of pump, and reservoir 204. In this configuration, the system may operate flow selector valve 202 to connect handpiece 110 with BSS fluid bottle 112, reservoir 204 or with pump 203 based on signals received from console 115 resulting from the surgeon's input to user interface 130.

The flow selector valve 202 illustrated in FIG. 2A provides a single input port and may connect port '0' to one of three available ports numbered '1', '2', and '3'. The exemplary embodiment is not limited to one flow selector valve, and may be realized using two flow selector valves each having at least two output ports, possibly connected together to provide the functionality described herein. For example, a pair of two output port valves may be configured in a daisy chain arrangement, where the output port of a first valve is directly connected to the input port of a second valve. Console 115 may operate both valves together to provide three different flow configurations. For example, using two valves, valve one and valve two, valve one may use output port one, which is the supply for valve two. Valve two may connect to one of two ports providing two separate paths. When valve one connects its input port to its second output port rather than the output port that directs flow to the second valve, a third path is provided.

It is also envisioned that flow selector valve 202 may be or comprise one or more pinch valves. The one or more pinch valves may be located along fluid pathway 221 and/or 223, or any other fluid pathway as discussed herein. Further, there may be one or more fluid pathways coupled with handpiece 110 and extending to various components of cassette 250, including a first fluid pathway from fluid vacuum sensor 201 to collector 206 via pump 203 and/or a second fluid pathway to reservoir 204. In another embodiment, fluid pathway 220 is a single fluid pathway that couples with fluid vacuum sensor 201. From fluid vacuum sensor 201, the single fluid pathway 220 may divide into two fluid pathways, one to collector 206 via pump 203 and one to reservoir 204. Further, one or more pinch valves and/or flow selector valve 202 may be located along the fluid pathway between fluid vacuum sensor 201 and collector 206 and/or between fluid vacuum sensor 201 and reservoir 204.

Thus while a single flow selector valve 202 is illustrated in FIG. 2A, it is to be understood that this illustration represents a flow selector valve arrangement, including one or more flow selector valves performing the functionality described herein, and is not limited to a single device or a single flow selector valve. In the exemplary fluid vacuum sensor 201, a strain gauge or other suitable component may communicate or signal information to console 115 to provide an amount of vacuum sensed in the handpiece fluid pathway 220. Console 115 may determine the actual amount of vacuum present based on the communicated information.

Fluid vacuum sensor 201 monitors flow into and out of the line, and can be used to determine when flow should be reversed, such as encountering a certain pressure level (e.g. in the presence of an occlusion), and based on values obtained from the fluid vacuum sensor 201, the system may control selector valve 202 and the pumps illustrated. It is to be understood that while components presented in FIG. 2A and other drawings of the present application are not shown connected to other system components, such as console 115, they are in fact connected for the purpose of monitoring and control of the components illustrated.

With respect to fluid vacuum sensor 201, emergency conditions such as a dramatic drop or rise in pressure may result in a type of fail-safe operation. The exemplary embodiment employs fluid vacuum sensor 201 to monitor the flow conditions and provide signals representing flow conditions to the system such as via console 115 for the purpose of controlling components shown including but not limited to flow selector valve 202 and the pumps shown. The fluid pathways or flow segments of surgical cassette system 200 may include the fluid connections, for example flexible tubing, between each component represented with solid lines in FIG. 2A.

Vacuum pump arrangement 207 is typically coupled with console 115, and may be connected with reservoir 204 via fluid pathway or flow segment 230. In the configuration shown, vacuum pump arrangement 207 includes a pump 208, such as a venturi pump and an optional pressure regulator 209 (and valve (not shown)), but other configurations are possible. In this arrangement, vacuum pump arrangement 207 may operate to remove air from the top of reservoir 204 and deliver the air to atmosphere (not shown). Removal of air from reservoir 204 in this manner may reduce the pressure within the reservoir, which reduces the pressure in the attached fluid pathway 226, to a level less than the pressure within eye 114. A lower reservoir pressure connected through flow selector valve 202 may cause fluid to move from the eye, thereby providing aspiration. The vacuum pump arrangement 207 and reservoir 204 can be used to control fluid flow into and out of reservoir 204.

The optional pressure regulator 209 may operate to add air to the top of reservoir 204 which in turn increases pressure and may force the air-fluid boundary 213 to move downward. Adding air into reservoir 204 in this manner may increase the air pressure within the reservoir, which increases the pressure in the attached fluid aspiration line 226 to a level greater than the pressure within eye 114. A higher reservoir pressure connected through flow selector valve 203 may cause fluid to move toward eye 114, thereby providing venting or reflux.

The exemplary embodiment may involve peristaltic operation, aspirating fluid from eye 114 to collector 206 illustrated in FIG. 2A, or venting fluid to the eye 114 to reduce the amount of pressure in the aspiration line (where such venting is only shown from BSS bottle 112 in FIG. 2A). Peristaltic pumping is generally understood to those skilled in the art, and many current machines employ peristaltic and/or venturi pumps as the vacuum or pressure sources. Generally, a peristaltic pump has fluid flowing through a flexible tube and a circular rotor with a number of rollers attached to the periphery of the circular rotor. As the rotor turns, fluid is forced through the tube. Venturi pumping, or aspiration or aspirator pumping, produces the vacuum using the venturi effect by providing fluid through a narrowing tube. Because of the narrowing of the tube, the speed at which the fluid travels through the tube increases and the fluid pressure decreases (the "Venturi effect"). As may be appreciated, operating pumps in one direction or another can change the pressure and the operation of the associated device, such as the operation of the cassette in the exemplary embodiment.

Figure 2B:
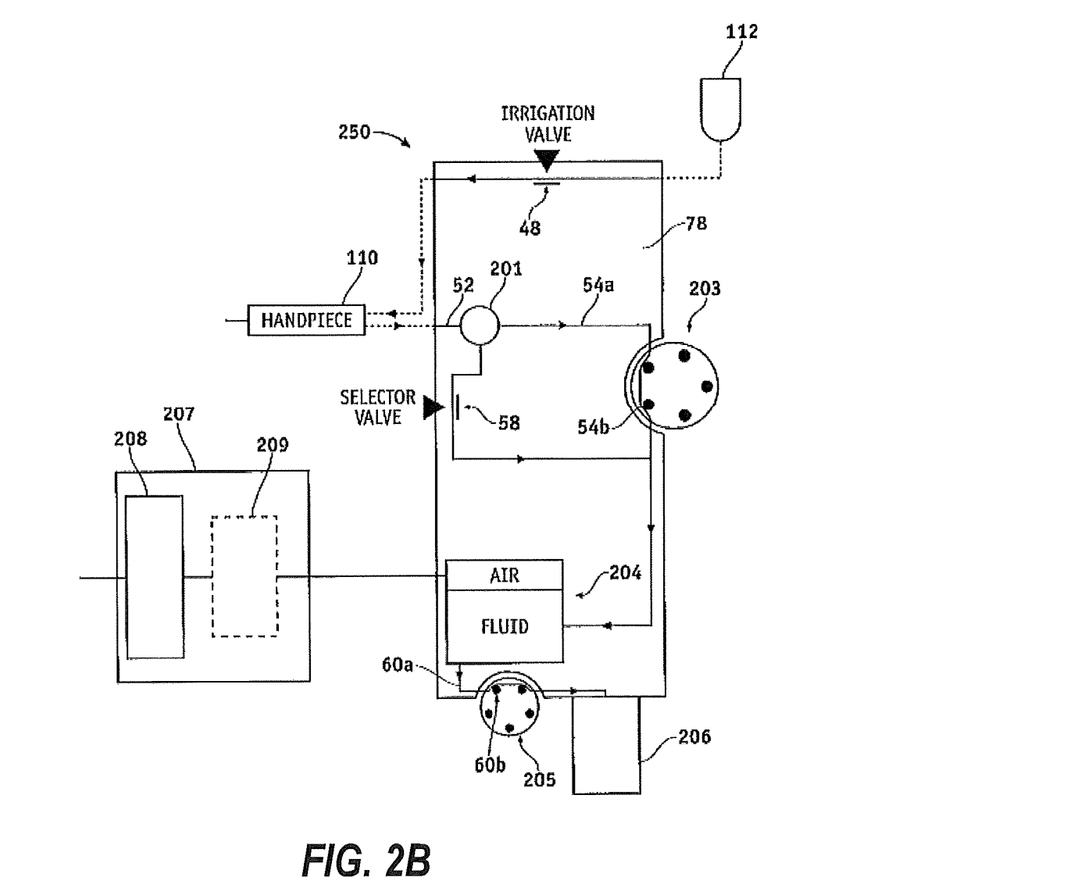
FIG. 2B is a functional block diagram of an exemplary cassette system for an eye treatment system under one embodiment.

Referring now to FIG. 2B, another system is illustrated. FIG. 2B generally highlights the surgical aspiration and irrigation fluid control elements included within the cassette 250 and console 115, with the irrigation components often being relatively straightforward. A BSS fluid bottle 112 of console 115 optionally provides irrigation fluid pressure control by relying at least in part on a gravity pressure head that varies with a height of BSS fluid bottle 112 or the like. An irrigation on/off pinch valve 48 may generally include a short segment of a flexible conduit of cassette 250, which can be engaged and actuated by an actuator of console 115, with a surface of cassette body 78 often being disposed opposite the actuator to facilitate closure of the conduit lumen. Alternative irrigation flow systems may include positive displacement pumps, alternative fluid pressurization drive systems, fluid pressure or flow modulating valves, as discussed above, and/or the like.

Aspiration flow path 52 couples an aspiration port in the tip of handpiece 110 with pump 203 and/or a reservoir 204. Fluid aspirated through handpiece 110 may be contained in reservoir 204 regardless of whether the aspiration flow is induced by pump 203 or vacuum pump arrangement 207. When valve 58 is closed and pump 203 is in operation, pumping of the aspiration flow may generally be directed by the pump, independent of the pressure in the reservoir 204. The aspiration flow may flow through conduit 54a. Conversely, if pump 203 is a peristaltic pump, when pump 203 is off, flow through the pump may be halted by pinching of the elastomeric tubing arc of the peristaltic pump by one or more of the individual rollers of the peristaltic pump rotor. Hence, any aspiration fluid drawn into the aspiration network (fluid pathways) when pump 203 is off will typically involve the opening of a selector control valve 58 so that the aspiration port of the probe is in fluid communication with reservoir 204. Alternatively, communication with vacuum pump arrangement 207 may be accomplished by disengaging the peristaltic probe drive from the elastomeric tubing. The pressure within reservoir 204 may be maintained at a controlled vacuum level, often at a fixed vacuum level, by vacuum pump arrangement 207. Vacuum pump arrangement 207 may comprise a vacuum (e.g. Venturi) pump, a rotary vane pump, a vacuum source, pressure regulator, or the like. Aspiration fluid that drains into reservoir 204 may be removed by pump 205 and directed to collector 206. Vacuum pressure at the surgical handpiece may be maintained within a desired range through control of the fluid level in reservoir 204.

Figure 2C:
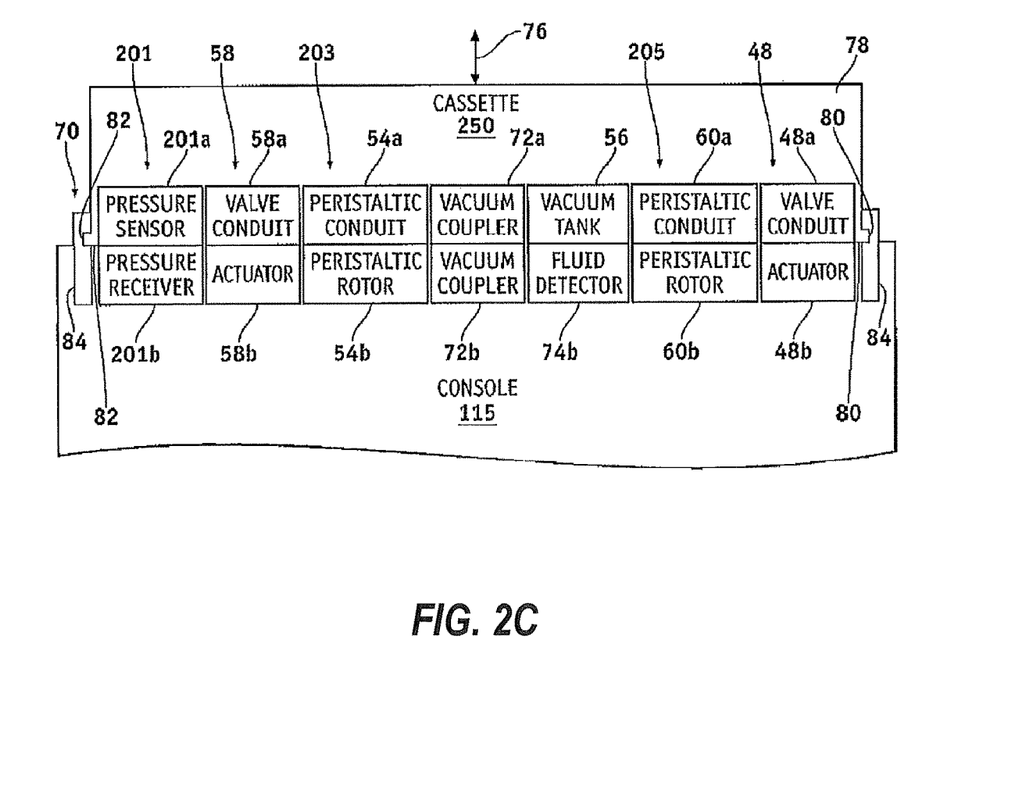
FIG. 2C is a schematic illustrating elements of a cassette and console as shown in FIG. 1A under one exemplary embodiment.

Referring now to FIG. 2C, an interface 70 between cassette 250 and console 115 is schematically illustrated. Many of the fluid network structures described above regarding FIGS. 2A and 2B include or make use of corresponding elements of cassette 250 and the console 115. For example, with respect to FIG. 2B, fluid vacuum sensor 201 may be included in a pressure sensing system which includes a pressure sensor 201a having a pressure chamber and a surface that moves in response to variations in the pressure in the chamber. Axial movement of the pressure sensor surface may be determined using a pressure receiver 201b. In the exemplary embodiments, direction of movement of the pressure sensor surface may be aligned with a mounting axis 76 of cassette 250, representing a direction of movement of cassette 250 during mounting of cassette 250 to console 115.

Similarly, selector valve 58 may make use of a resilient valve conduit 58a in cassette 250 that is engaged by an actuator 58b of console 115. As described above, pump 203 may include a conduit 54a of cassette 250 engaged by a peristaltic rotor 54b of console 115, with the interface 70 effecting engagement between the conduit 54a and the peristaltic rotor 54b. A vacuum coupler 72a of cassette 250 may engage a vacuum coupler 72b of console 115 so as to allow vacuum pump arrangement 207 to apply a vacuum to reservoir 204 (See FIG. 2B). Vacuum tank 56 may be coupled with a fluid detector 74b of console 115 using a mechanical, electrical, or light fluid presence detector system so as to allow controller 125 of console 115 to determine when it is appropriate to energize pump 205. Rather than simply detecting the presence of fluid, alternative embodiments might employ a more complex fluid level sensing system which determines a quantity or volume of fluid in the tank for purposes of selectively energizing pump 205. Pump 205 includes a conduit 60a of cassette 250 and a peristaltic rotor 60b of console 115. Irrigation valve 48 may include a resilient valve conduit 48a of cassette 250 and a valve actuator 48b of console 115.

Engagement and alignment between cassette 250 and the interfacing structures of console 115 may be achieved through a variety of mechanisms, some of which are described in U.S. Pat. No. 8,491,528 to Muri et al., titled "Critical Alignment of Fluidics Cassettes" issued Jul. 23, 2013 and U.S. Pat. Pub. No. 2010/0249,693 to Jeremy T. Links, titled "Cassette Capture Mechanism," filed Mar. 31, 2009, each of which are incorporated by reference in their entirety herein. A cassette 250 may generally have a height and a width which generally are greater than a thickness of cassette 250 along a mounting axis, allowing the interfacing fluid pathway network elements of cassette 250 and corresponding components of console 115 to be distributed in a roughly planar configuration. In addition to the individual interfaces, cassette 250 may generally include a cassette body 78 with positioning surfaces 80 and 82 that engage corresponding cassette receptacle surfaces 84 of console 115. Cassette receptacle surfaces 84 define a cassette receptacle area that receives and positions cassette 250. In one exemplary embodiment, cassette 250 is manually supported and advanced along mounting axis 76 until positioning surfaces 80 engages and deflects an alignment switch of console 115. One or more alignment switches may be used; preferably two alignment switches are employed with a cassette receptacle on console 115. The alignment switch may be a pin/flag, optical, magnetic, or any other detection mechanism known in the art.

In certain embodiment, the present disclosure provides a plurality of techniques for detecting the use and/or depletion of an irrigation source. As will be discussed in greater detail below, one exemplary technique comprises the utilization of time and flow processing, where depletion is measured based on an initial volume and an approximate use of irrigation fluid over time. Another exemplary technique comprises the use of optical or resistive flow detection, where irrigation fluid depletion is calculated through optical and/or resistive sensors. In another exemplary technique, gravimetric detection may be utilized, where depletion is measured based on an initial volume and the weight of the irrigation fluid source or waste over time. In a still further exemplary technique, pressure detection may be utilized to measure depletion based on pressure exerted by the irrigation fluid upon a pressure sensor.

The detection of irrigation fluid is somewhat unique in that the solution itself is formulated such that very few or preferably none of the components within the solution are foreign to a human eye, and thus should have no pharmacological action. A typical irrigation solution may comprise a balanced salt solution, which is a sterile intraocular irrigating solution for use during intraocular surgical procedures, including those requiring a relatively long intraocular perfusion time (e.g., pars plana vitrectomy, phacoemulsification, extracapsular cataract extraction/lens aspiration, anterior segment reconstruction, etc.). As the solution typically will not contain preservatives, it is usually prepared just prior to use in surgery.

An exemplary irrigation solution mix may comprise two parts, where Part I comprises a sterile solution in a single-dose bottle to which the Part II concentrate is added. For example, a 250 mL single-dose bottle may comprise a sterile 240 mL solution. The Part I solution may contain: sodium chloride, potassium chloride, dibasic sodium phosphate, sodium bicarbonate, hydrochloric acid and/or sodium hydroxide (to adjust pH), in water for injection. For a 250 mL single dose bottle, exemplary amounts may comprise 7.44 mg sodium chloride, 0.395 mg potassium chloride, 0.433 mg dibasic sodium phosphate, and 2.19 mg sodium bicarbonate.

Part II may be a sterile concentrate in a single-dose vial for addition to Part I. Continuing with the example directed to the 250 mL single-dose bottle, the Part II single-dose vial may comprise 10 mL of the sterile concentrate. The Part II concentrate may comprise calcium chloride, magnesium chloride hexahydrate, dextrose, glutathione disulfide (oxidized glutathione) in water for injection. Exemplary amounts may comprise 3.85 mg calcium chloride dihydrate, 5 mg magnesium chloride hexahydrate, 23 mg dextrose, and 4.6 mg glutathione disulfide. Continuing with the example, after addition of Part II concentrate to the Part I bottle, exemplary amounts of the reconstituted product may contain sodium chloride (7.14 mg), potassium chloride (0.38 mg), calcium chloride dihydrate (0.154 mg), magnesium chloride hexahydrate (0.2 mg), dibasic sodium phosphate (0.42 mg), sodium bicarbonate (2.1 mg), dextrose (0.92 mg), glutathione disulfide (oxidized glutathione) (0.184 mg), hydrochloric acid and/or sodium hydroxide (to adjust pH), in water for injection. The reconstituted product may have a pH of approximately 7.4. Osmolality may be approximately 305 mOsm.

It is understood by those skilled in the art that the above example is provided for illustrative purposes only, and that other solutions and product amounts suitable for phacoemulsification are contemplated by the present disclosure.

There are many factors that influence flow rates in a phaco machine, including IV pole height, pump speed and valving, among others. As illustrated in FIG. 1B, a pressure supply line 160 may be provided from a surgical console to at least one irrigation source 151. The pressure supply line 160 may provide any pressure desired by the user up to a maximum available pressure, and may use air or any specific gas to provide the increase or modification in pressure in at least the irrigation source 151.

Pressure supply line 160 may be connected to the lower end of the irrigation source 151 such that pressurization of the irrigation source 151 is accomplished by gas being delivered through the pressure supply line 160, whereupon gas passes through any remaining irrigation fluid in the irrigation source 151 and into a pocket of gas above the irrigation fluid. Such a connection to the lower end of the irrigation source 151 may be made through an IV spike, for example. In this way, for example, the pressure supply line may be suitable for use with any size irrigation source.

Additionally and alternatively, pressure supply line 160 may terminate at the top, or highest point, within the irrigation source, to allow for the dispensing of the pressurized gas with little to no interaction with the body of the irrigation fluid within the irrigation source 151. This form of delivery may decrease or eliminate the interaction of the delivered gas with the irrigation fluid, and may thus further decrease turbidity associated with the introduction of a pressurized gas.

As discussed above, delivery of irrigation fluid may occur through line 156, which may begin at the lower end of the irrigation source 152 and may terminate at or into the surgical system controller at fluidics panel 154 and to handpiece 158. In an embodiment of the present invention, both the pressure supply line 160 and the irrigation delivery line 156 may be in fluidic communication with the irrigation source through an IV spike. For example, the surgical system controller may include pressure fittings for each of the pressure supply line 160 and the irrigation delivery line 156. Further, an IV spike compatible for use with two lines may be constructed to withstand the increase in pressure provided by the system, and may include valves or backflow prevention mechanisms to allow for reduction of pressure in, for example, the pressure supply line without the irrigation fluid entering the pressure supply line 160.

In an embodiment of the present invention, the pressurized gas may be limited to a low pressure or low maximum available pressure, and may be constant so as to provide a stable and non-dynamic pressure to the irrigation source. For example, the pressure delivered through the pressure supply line 160 may be set by a regulated air source which may have a range of 0 to about 5 PSI. As would be appreciated by those skilled in the art, a maximum available pressure may be controlled electronically or through limiting the size of the pressurization device which may be, for example, a compressor. Likewise, a threshold monitoring may be performed, or a metered pressurization, for example, to limit pressure below an acceptable maximum. The pressure resulting in the delivery line may be measured within the surgical system controller and may be controlled by a user of the system, as discussed herein.

In one embodiment, the resultant pressure within the irrigation delivery line 156 may thus be controlled by adjusting both the height of the irrigation source 151 and the pressure introduced into the irrigation source 151 through the pressure supply line 160. For example, an IV pole may be raised in conjunction with the addition of pressure into the irrigation source 151, to thereby increase the overall pressure of the fluid being delivered to the surgical system controller and ultimately to the surgical site. Such a combination may allow for a more stable pressurized delivery of irrigation fluid by combining a constant minimum pressure through the pressure supply line 160 and dynamic pressure control through the changing of the irrigation source height. Such a blended approach may allow for more control over the pressure delivered during a surgical procedure, may reduce or eliminate unwanted pressure spikes or reduction in pressure due to vacuum buildup, and may allow for a reduced equipment zone by allowing for the use of shorter irrigation source heights, such as using a relatively short IV pole. Further, the increase of pressure which may be achievable using the present invention may provide the user with pressure sufficient to achieve a Tamponade feature if, for example, during surgery a retinal hemorrhaging arises.

An estimation of flow rate from irrigation source 151 may be calculated using the various factors discussed above (e.g., IV pole height, pump speed, valving, pressure). Based on a configuration of host settings for a volume of the initial irrigation source, the system may provide various levels of warnings or errors based on a volume or percentage of irrigation fluid used. One advantage of this approach is that additional hardware is not required, and thresholds for various warnings and/or errors could be set conservatively to accommodate estimation factors.

In one embodiment, a fluid sensor or arrangement of sensors may be deployed at any point, or multiple points of the system fluid delivery path. Fluid sensors may comprise level sensors (e.g., probe sensor, float sensor, magnetic sensor, resistive sensor, capacitive sensor), for sensing fluid levels in irrigation source 151, or may comprise flow level sensors for sensing fluid flow through any point or points within the system. In the case of fluid level sensors, fluid levels may be detected in irrigation source 151, and if a low-level fluid condition is detected, a suitable alarm or warning may be triggered.

Figure 3A:
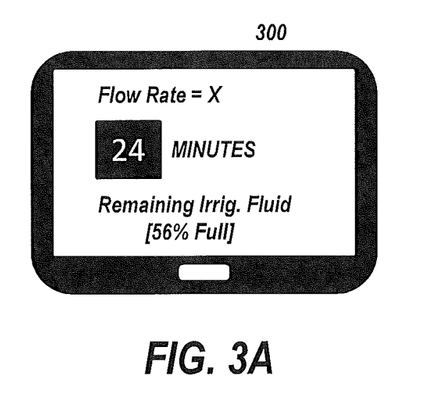
FIGS. 3A-B illustrate exemplary presentations of irrigation fluid flow over time and indication of remaining fluid capacity under one embodiment.
Figure 3B:
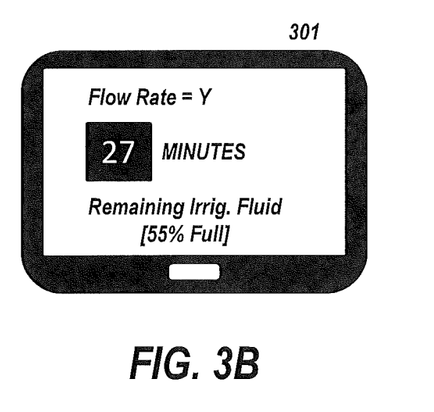

In one embodiment, flow sensors may be utilized in one or more points within the system. Flow sensors may be advantageous in that the sensors may be integrated into the system, thus allowing conventional irrigation fluid containers to be used without modification. Furthermore, as flow sensors are dependent upon the actual use of the irrigation fluid, irrigation fluid status and advanced warnings may be provided as illustrated in FIGS. 3A and 3B. For example, if one or more flow sensors detect a heavier flow of irrigation fluid being used during a procedure, the processor in the system may calculate a remaining use time and display 300 the time (e.g., "24 minutes of remaining irrigation fluid supply") so that personnel can quickly determine if adjustments to the procedure may be necessary. If the irrigation fluid in use is reduced in response to the notification, the system processor may automatically update 301 the time accordingly (e.g., "27 minutes of remaining irrigation fluid supply").

Figure 4:
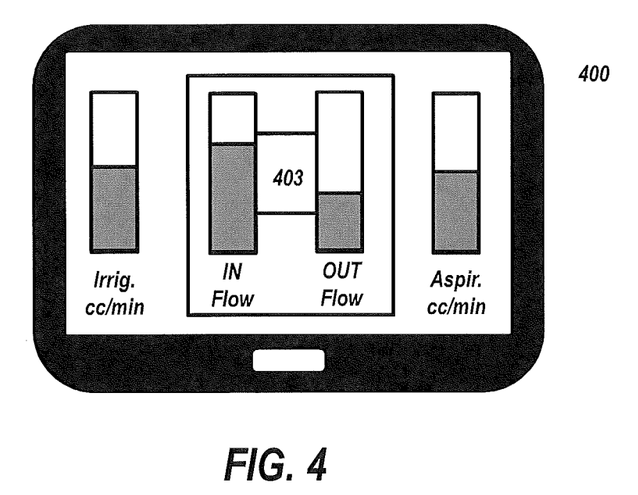
FIG. 4 illustrates an exemplary presentation of a fluid control panel comprising detected irrigation and aspiration amounts/flow, inflow, outflow, and fluid balance under one embodiment.

Furthermore, a general flow control panel may be provided on display 159 and is illustrated in one embodiment in FIG. 4. Here, the various sensor flow measurements are displayed 400 to show irrigation flow (e.g., cc/min) and aspiration flow (cc/min). Furthermore, an inflow and outflow display may be provided, together with a fluid balance indicator 403. Inflow fluid may originate in the irrigation bottle and travels from the irrigation bottle through plastic tubing, into the phaco needle (158) and finally into the anterior chamber of the eye. To create a pressure gradient, the bottle may be placed at a height above the patient. When the pinch valve is open the fluid in the bottle and tubing creates pressure in the anterior chamber. As an example, approximately 11 mm Hg pressure (above ambient atmospheric pressure) may be produced intraocular for every 15 cm (6 inches) bottle height above the patient's eye. Outflow fluid may be fluid that leaves the anterior chamber. Fluid leaves through the phaco needle into the tubing and into the anterior chamber of the eye. This can be increased by increasing the aspiration flow rate. On occasion, fluid loss may occur through wound leakage.

Fluid balance may be determined from the pressure gradient and is considered "balanced" when adequate pressure is available to keep up with the outflow. This balance maintains a stable anterior chamber by keeping the pressure in the anterior chamber fairly constant. If the balance of inflow and outflow is altered, the anterior chamber can be under or over-pressurized. If under pressurized this can lead to shallowing and/or collapse on the anterior chamber. This will cause forward movement of the iris, lens and posterior capsule. This may lead to inadvertent rupture of the posterior capsule, due to its movement towards the phaco needle. Over pressurization (bottle height too high) can cause misdirection of aqueous fluid or deepening of the anterior chamber with zonular stress. As shown in FIG. 4, a pressure balance range 403 may be calculated and displayed, where ranges outside the range may trigger an alarm or warning.

It should be understood by those skilled in the art that the embodiments of FIGS. 3A-4 are just one example, and that a variety of modifications are contemplated in the present disclosure. For example, the embodiments may be combined on one screen, and may be further combined with other displays relating to system operation or system parameters. The graphical displays may be provided in any format, such as bar graphs, pie graphs, charts, line plots etc., and may be part of a system "dashboard" displaying flow parameters.

In one embodiment, one or more electrical fluid sensors may be used, where sensor connection points may be at any or all points in an irrigation fluid path. Exemplary sensor connection points include (1) between irrigation source 151 and drip chamber spike 152, (2) integrated into tubing cassette 154 and fluidics panel 153, (3) between handpiece irrigation line 156 and handpiece 158, (4) between handpiece 158 and handpiece aspiration line 157, and/or (5) between fluidics panel 153 and waste collection bag 155.

It should be noted that careful consideration should be had for sensor connections from handpiece 158 to waste collection bag 155, as aspiration flow may not be consistent, and/or may experience fluid loss during a surgical procedure. Nevertheless, these general inconsistencies may be compensated for by having the system continuously monitor aspiration flows together with irrigation flows. By calculating an average differential between aspiration and irrigation flows, a weighted flow value may be calculated and applied to the aspirational flow to ensure relative consistency. Such a configuration may be advantageous, for example, to determine circumstances or procedures that may experience heavy fluid loss or other anomalies in the aspiration flow.

In one exemplary embodiment, one or more optical fluid sensors may be utilized at any or all points in an irrigation fluid path. Exemplary optical sensor connection points include, (1) proximate to irrigation source 151, (2) proximate to drip chamber spike 152. (3) proximate to irrigation tubing between drip chamber spike 152 and tubing cassette 154, (4) integrated into tubing cassette 154 and fluidics panel 153, (5) proximate to handpiece irrigation line 156, (6) proximate to handpiece aspiration line 157, and/or (7) proximate to waste collection bag 155.

Similar to electrical fluid sensors, careful consideration should be had for optical sensor connection from handpiece 158 to waste collection bag 155, as aspiration flow may not be consistent, and/or may experience fluid loss during a surgical procedure. Accordingly, similar monitoring of aspiration flows together with irrigation flows may be enabled to calculate a weighted differential as described above.

In another exemplary embodiment, gravimetric sensors may be utilized to detect fluid. Based on an initial weight and volume of fluid, subsequent volume may be detected by sampling weight of an irrigation source during use. For example, at an irrigation solution of 9 grams of salt per liter, a liter of fluid would weight approximately 1,004.6 grams. Accordingly, a 500 ml bottle would contain 502.3 grams or 17.7181 ounces of saline solution. In this example, a load cell or similar weighing device may be mounted on an IV pole hanger (150) such that an irrigation fluid container would be suspended from the weighing device. The weighing device is preferably configured to communicate via wired or wireless communication to the system. As a depletion of fluid would result in a decrease in weight of the irrigation fluid, these sensed values may be utilized by the system to calculate overall irrigation fluid depletion.

Alternately, the load cell or weighing device may be mounted in fluidics panel 153 to weigh the contents of waste collection bag 155. In this example, the increase in weight for the waste collection bag would indicate a level of fluid depletion. As was discussed above, fluid received in waste collection bag 155 may not necessarily correlate exactly to the fluid initially contained in the irrigation container. Accordingly, the system processor may be programmed to apply a weight to the waste collection bag measurement value to more accurately determine irrigation fluid depletion. In another embodiment, measurements may be taken from both the irrigation source and the waste bag to increase accuracy and provide a fault-tolerant system that accounts for fluid leakage.

In another exemplary embodiment, pressure sensors may be utilized to detect fluid depletion by measuring/sensing the fluid pressure exerted upon a sensor. Based on the height of an IV pole hanger, the fluid height may exert a given pressure that may decrease proportionately to the height of the fluid remaining. A pressure sensor inside fluidics panel 153 may be used to estimate a head height of the remaining fluid.

Figure 5:
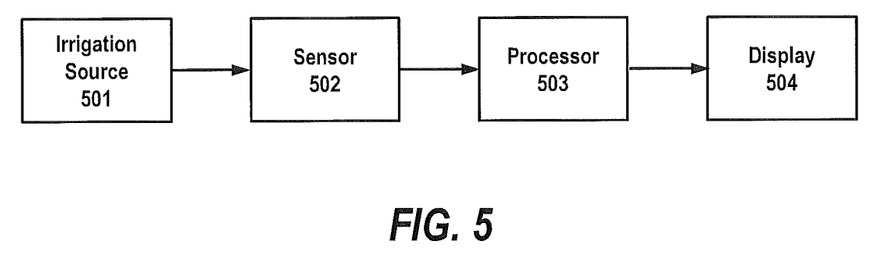
FIG. 5 illustrates an exemplary simplified block diagram for sensing and processing fluid volume/flow.

FIG. 5 illustrates an exemplary block diagram embodying any of the examples provided herein, wherein volume/flow from an irrigation source 501 is sensed in a sensor 502, where sensed values or readings are provided to processor 503, which may be a surgical device processor. Processor 503 is configured to perform various fluidics and/or volumetric processing, and forwards processed results for presentation on display 504. Additionally, processor 503 may be configured to generate warnings and alarms commensurate with the processed data.

Figure 6:
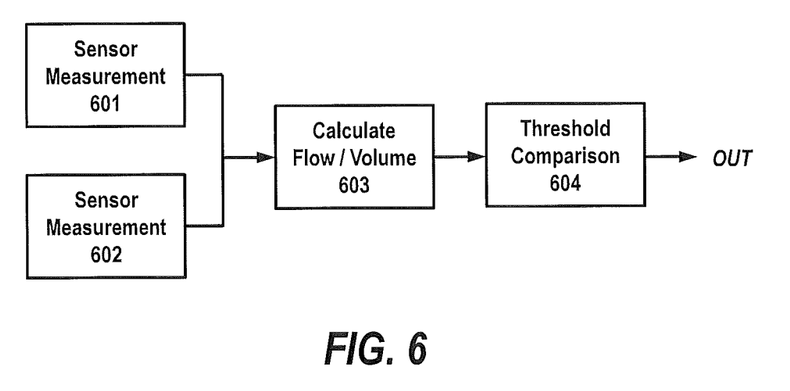
FIG. 6 illustrates an exemplary flowchart for processing multiple sensor readings and performing threshold comparison to determine is volume/flow is within acceptable predefined limits.

FIG. 6 illustrates a multi-sensor arrangement in one embodiment, where sensor measurements 601 and 602 are provided to a processor for flow/volume processing and calculation 603. Processed readings may further be subjected to threshold comparison 604 in the processor to determine if sensor readings are within acceptable, predetermined, limits. If readings are determined to be outside predetermined limits an output signal (OUT) may be generated to indicate an alert or warning.

Those of ordinary skill in the art may recognize that many modifications and variations of the herein disclosed systems and methods may be implemented without departing from the spirit or scope of the invention. Thus, it is intended that the present invention covers such modifications and variations provided they come within the scope the appended claims and their equivalents.

For example, multiple different sensors may be applied in detecting fluid depletion. Additionally, the applications disclosed herein are not necessarily limited strictly to phacoemulsification processes, but may be applied to pressurized infusion ophthalmic surgery, and other similar surgeries as well. Other applications may include medical applications, such as an interlock between an irrigation fluid source and power delivered to a drill, saw, laser or other surgical, procedural or dental device, and/or detection of fluid delivery in a therapeutic device (e.g., cooling or warming device). Further applications include petro-chemical applications, such as detecting of product delivery interruption in a pipeline or other fluid delivery system, or interlock between a fluid source and the power delivered to a pump or motor.

Further applications may include process monitoring, such as detection of interruptions in the delivery of a liquid component or components necessary for a given chemical process, or detection of interruption in the delivery of a cooling or warming agent necessary for a given chemical process. A still further application may include water delivery or treatment, such as interlock between a water source and power delivered to a pump or motor, or detection of water interrupts between stages of water delivery or treatment.

What is claimed is:

1. A surgical system, comprising:
a surgical console comprising a display;
a processor operatively coupled to the surgical console;
a vacuum pump arrangement;
a surgical cassette in fluid communication with an irrigation source and an aspiration line, the surgical cassette comprising a reservoir within a fluid path of the aspiration line;
at least one flow sensor; and
a volume sensor comprising a pressure sensor, a gravimetric sensor, or a level sensor,
wherein the processor is configured to:
 determine a volume of fluid in the irrigation source from the volume sensor,
 receive, from the at least one flow sensor, sensed measurements regarding a rate of fluid flow over time from the irrigation source, and
 process the rate of fluid flow relative to the determined volume, and produce a first signal for the display to indicate a remaining capacity of the volume of fluid,
wherein a pressure sensed by the pressure sensor is determined based on a height of a fluid in the irrigation source and the processor determines the volume of fluid in the irrigation source based on the pressure sensed by the pressure sensor when the volume sensor comprises the pressure sensor,
wherein the vacuum pump arrangement is configured to add air to the reservoir and remove air from the reservoir to regulate pressure within the reservoir.

2. The surgical system of claim 1, wherein the processor is configured to produce a second signal for the display indicating a time period before depletion of the irrigation source fluid relative to the sensed rate of fluid flow.

3. The surgical system of claim 1, wherein the processor is configured to produce a warning signal if the remaining capacity of the volume of fluid is below at least one threshold.

4. The surgical system of claim 1, wherein the at least one flow sensor comprises at least one of an electrical sensor, an optical sensor, a resistive sensor, and a pressure detector.

5. The surgical system of claim 4, wherein the sensed measurements are received in the processor from the at least one flow sensor sensing flow rates from one or more points in the surgical system, the one or more points comprising at least one of a drip chamber spike, a tubing cassette, a fluidics panel, a handpiece, a handpiece irrigation line, a handpiece aspiration line, a waste collection bag and the irrigation source.

6. The surgical system of claim 1, wherein the processor is configured to receive sensed measurements regarding a rate of fluid flow over time from the aspiration line, process the rate of fluid flow from the aspiration line relative to the rate of fluid flow from the irrigation source and produce a third signal for the display to indicate the processed rate of fluid flow from the aspiration line relative to the rate of fluid flow from the irrigation source.

7. The surgical system of claim 6, wherein the processor is configured to process the rate of fluid flow from the aspiration line by applying a weight to the sensed measurements regarding the rate of fluid flow over time from the aspiration line.

8. The surgical system of claim 1, wherein the irrigation fluid comprises a balanced salt solution.

9. The surgical system of claim 1, wherein the processor is configured to determine a fluid balance for the surgical system based at least in part on the rate of fluid flow over time.

10. The surgical system of claim 1, wherein the volume sensor is further present in a waste collection bag or inside a fluidics panel.

11. The surgical system of claim 1, wherein the level sensor comprises at least one of a probe sensor, a float sensor, a magnetic sensor, a resistive sensor, or a capacitive sensor.

12. A processor-based method for operating a surgical system comprising a surgical console comprising a display, a processor operatively coupled to the surgical console, a surgical cassette in fluid communication with an irrigation source and an aspiration line, the surgical cassette comprising a reservoir within a fluid path of the aspiration line, a vacuum pump arrangement, at least one flow sensor, and a volume sensor, the method comprising:
   determining in the processor a volume of fluid in the irrigation source from one or more signals received from the volume sensor;
   receiving in the processor, from the at least one flow sensor, sensed measurements regarding a rate of fluid flow over time from the irrigation source;
   processing the rate of fluid flow relative to the determined volume; and
   producing a first signal for the display to indicate a remaining capacity of the volume of fluid, wherein
   the volume sensor comprises a pressure sensor, a gravimetric sensor or a level sensor,
   a pressure sensed by the pressure sensor is determined based on a height of a fluid in the irrigation source and the processor determines the volume of fluid in the irrigation source based on the pressure sensed by the pressure sensor when the volume sensor comprises the pressure sensor and
   the vacuum pump arrangement is configured to add air to the reservoir and remove air from the reservoir to regulate pressure within the reservoir.

13. The processor-based method of claim 12, further comprising producing, in the processor, a second signal for the display indicating a time period before depletion of the irrigation source fluid relative to the sensed rate of fluid flow.

14. The processor-based method of claim 12, further comprising producing, in the processor, a warning signal if the remaining capacity of the volume of fluid is below at least one threshold.

15. The processor-based method of claim 12, wherein the at least one flow sensor comprises at least one of an electrical sensor, an optical sensor, a resistive sensor, and a pressure detector.

16. The processor-based method of claim 15, wherein the sensed measurements are received in the processor from the at least one flow sensor sensing flow rates from one or more points in the surgical system, the one or more points comprising at least one of a drip chamber spike, a tubing cassette, a fluidics panel, a handpiece, a handpiece irrigation line, a handpiece aspiration line, a waste collection bag and the irrigation source.

17. The processor-based method of claim 12, further comprising
   receiving sensed measurements regarding a rate of fluid flow over time from the aspiration line;
   processing the rate of fluid flow from the aspiration line relative to the rate of fluid flow from the irrigation source; and
   producing a third signal for the display to indicate the processed aspiration fluid flow relative to the irrigation fluid flow.

18. The processor-based method of claim 17, wherein processing the rate of fluid flow from the aspiration line comprises applying a weight to the sensed measurements regarding a rate of fluid flow over time from the aspiration line.

19. The processor-based method of claim 12, wherein the irrigation fluid comprises a balanced salt solution.

20. The processor-based method of claim 12, further comprising determining a fluid balance for the surgical system based at least in part on the rate of fluid flow over time.

* * * * *